United States Patent [19]

Braun et al.

[11] Patent Number: 4,522,591
[45] Date of Patent: Jun. 11, 1985

[54] ARTICULATOR FOR HOLDING DENTAL MODELS

[75] Inventors: Frank D. Braun, Düsseldorf; Walter Witt, Cologne; Stanislav Putra, Solingen, all of Fed. Rep. of Germany

[73] Assignee: IPCO Corporation, White Plains, N.Y.

[21] Appl. No.: 483,556

[22] PCT Filed: Aug. 7, 1982

[86] PCT No.: PCT/EP82/00168
§ 371 Date: Apr. 11, 1983
§ 102(e) Date: Apr. 11, 1983

[87] PCT Pub. No.: WO83/00431
PCT Pub. Date: Feb. 17, 1983

[30] Foreign Application Priority Data

Aug. 11, 1981 [DE] Fed. Rep. of Germany ....... 3131689

[51] Int. Cl.$^3$ .............................................. A61C 11/00
[52] U.S. Cl. ..................................................... 433/60
[58] Field of Search ........................ 433/60, 61, 62, 64

[56] References Cited

U.S. PATENT DOCUMENTS 565,326  8/1896  Bragg ................................... 433/64
2,571,280 10/1951  Naggi ................................... 433/60

Primary Examiner—Robert Peshock
Attorney, Agent, or Firm—Jones & Askew

[57] ABSTRACT

Articulator (1) for holding dental models with a stationary base (2) for the lower jaw model and an upper part (3) which is attached thereto in such a way that it can be swiveled, for holding the upper jaw model, with mountings (11, 12) in the upper part and the base for the jaw models, the mounting (11) for the upper jaw model being designed in such a way that it can be adjusted at random along three planes perpendicular to each other and can also be locked in any of the positions, and with the mountings (11, 12) being arranged such that the distance between them can be adjusted and locked.

6 Claims, 9 Drawing Figures

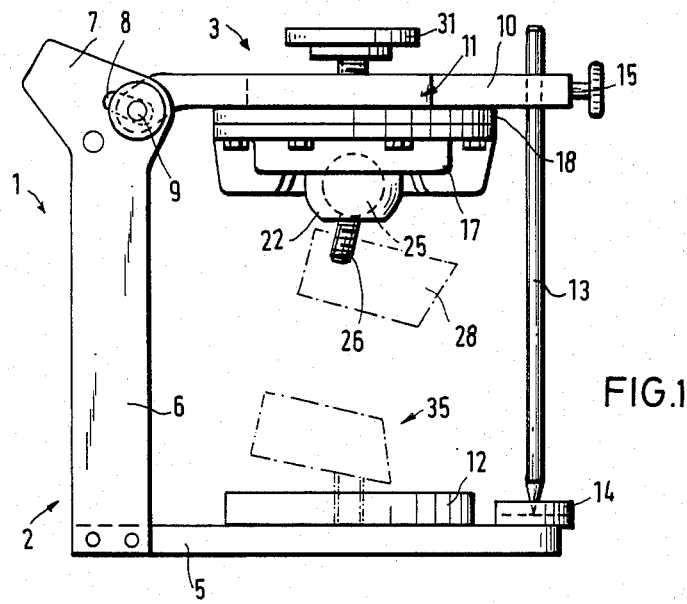
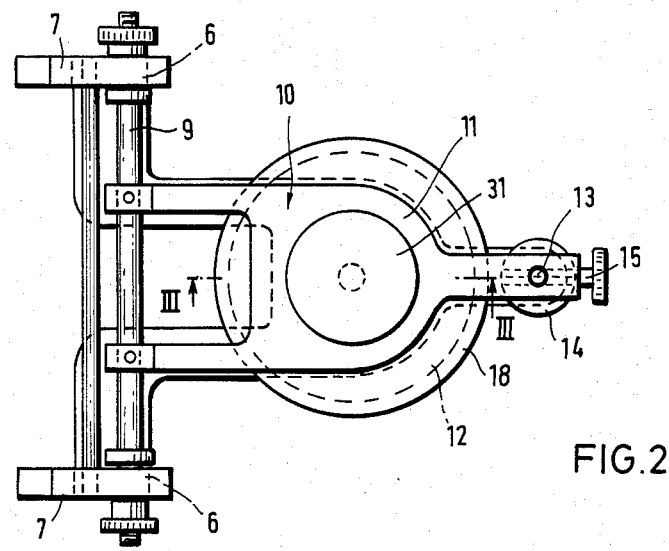

ARTICULATOR FOR HOLDING DENTAL MODELS

The subject of this invention is an articulator for mounting dental models with a stationary base for the lower jaw model and an upper part, which is attached thereto in such a way that it can be swiveled, for holding the upper jaw model, with mountings in the upper part and in the base for the jaw models.

Articulators of very different types are already known. By holding the dental models, these are devices which make it possible to reproduce the movement of the jaws with respect to each in the best possible manner. The model of the upper jaw is attached to the swiveling upper part of the articulator and the model of the lower jaw is attached to the stationary base, both models consisting of a cast reproduction of the teeth. The models are attached by means of, e.g., metal plates or other fasteners which can be detached on the lateral face of the articulator and which are preferably cemented into the lateral face of the cast. The alignment of the two dental models in the articulator is achieved by first taking the bite in wax, which is then placed between the two dental models in such a way that the teeth of these casts are aligned with respect to each other in the same way as they are in the mouth of the patient, however with the plaster material for attaching the metal plate still being soft enough to enable the alignment of the casts in the articulator. In the position wherein the areas are aligned with each other according to the bite taken, the two dental models are allowed to set until the plaster has dried. Subsequently, it is possible to work on the tooth models in the articulator. These well-known articulators have disadvantages insofar as cementing in the tooth models in connection with the metal plates requires too much work and time. Furthermore, the tooth models thus aligned with each other are restricted to use in the particular articulator and cannot be used in any other articulator; this makes it necessary to always send the jaw models, if required, together with the articulator employed, e.g., from the dental laboratory to the dentist and vice versa, a fact which is inconvenient as well as expensive.

It is therefore the goal of this invention to avoid the disadvantages mentioned above and to create an articulator in which the jaw models can be mounted without the use of plaster, thus making possible a random transfer from one articulator to the next.

According to this invention, this goal is achieved by the fact that the mounting for the maxillary model is designed such that it can be randomly adjusted in three planes perpendicular to each other and such that it can be locked into position in each of the positions. By thus designing the mounting as described by this invention, it is possible to always obtain an accurate coordination of the two jaws relative to each other by means of the bite taken in wax. This means that the fasteners for the jaw models are no longer attached to the models in such a way that they are dependent upon the articulator; instead, the shape and attachment of these fasteners is such that the models can be accurately fitted into each articulator without restricting the coordination of the models relative to each other to one particular articulator, but rather allowing in accurate adjustment of these models to be undertaken in any articulator designed according to this invention. This also renders the timecomsuming plaster casting heretofore required superfluous. Moreover, it is no longer necessary to ship the jaw models along with the articulator; instead it suffices to ship the jaw models only, since due to the free mobility of the upper mounting and the adjustability of the height of the mountings to each other it is possible to locate the exact jaw position with accuracy. The articulator can then be locked into this precise position.

Furthermore, this invention also refers to a device for the production of a dental-mechanical working model, such as is described in detail in German Patent Application P 28 56 963.3, and to this extent reference is made to the full scope and spirit of this patent application. The invention provides that the internal wall of the base and the back wall thereof enclose an approximately parabolic horizontal plate which is designed such that, relative to the lower edge of the base, it is staggered upward and in whose lower surface a permanent magnet is placed. Thus, it is possible to easily attach the subsequently remove the base together with the dental models contained therein in the articulator since, in the space between the plate and the lower edge, the shoe of the mounting according to this invention is inserted and locked into position by means of the magnet. Further advantageous practical examples of the device according to this invention are described in the subclaims 18 and 19.

The invention is discussed in greater detail by means of the practical examples represented in the drawings. It can be seen that:

FIG. 1 shows a lateral view of an articulator according to this invention,

FIG. 2 shows a horizontal projection of the articulator according to FIG. 1,

Figure 4:
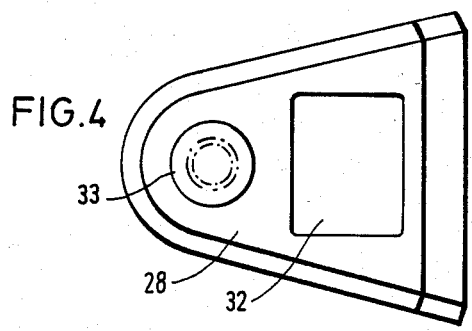
Figure 5:
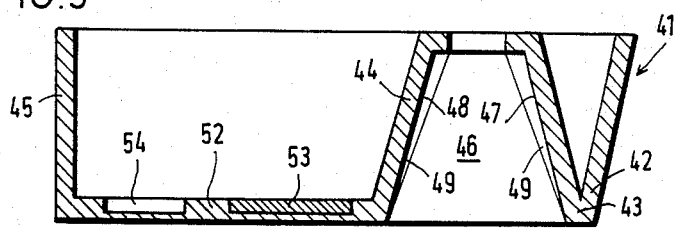
Figure 6:
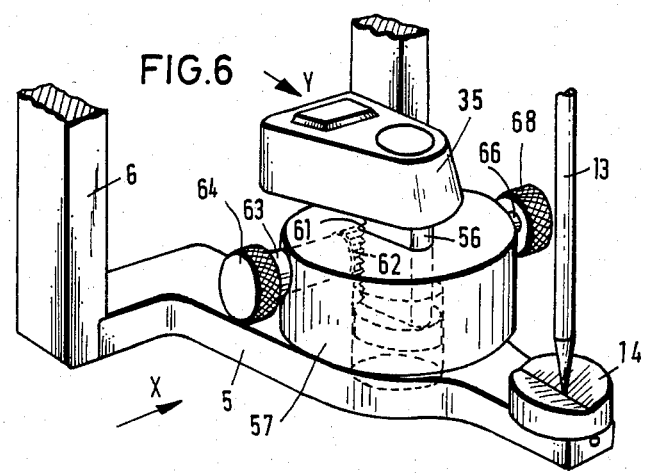
Figure 7:
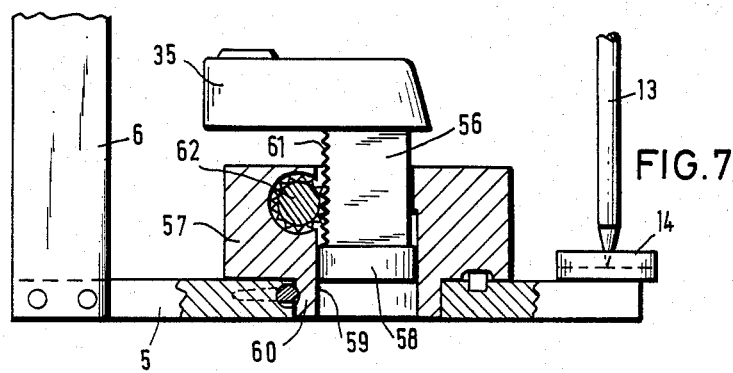
Figure 8:
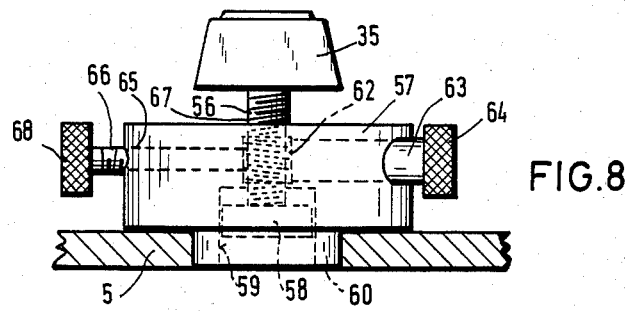
Figure 9:
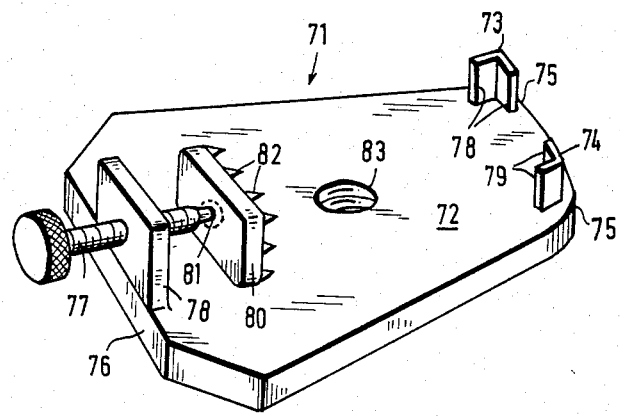

FIG. 4 shows a view from below onto the shoe of the articulator according to FIG. 1, FIG. 5 shows a picture of a device according to this invention for the manufacture of a dental-technical model, FIG. 6 shows a perspective view of the base of the device according to this invention, FIG. 7 shows a lateral view, partially cut, of the base according to FIG. 6 in the direction of the arrow X, FIG. 8 shows a view according to arrow Y in FIG. 6, and FIG. 9 shows a view of an example of a mounting plate according to this invention.

An articulator 1 according to this invention consists of a base 2 and an upper structure 3. The upper structure 3 is connected to the base 2 by means of a joint 4 such that it can be swivelled. The base 2 consists of a base plate 5, on both ends of which two supporting braces 6 can be seen. At the upper ends of the supporting braces 6, bearing extensions 7 are provided which have oblong holes 8 which hold a bearing axle 9 of the upper structure 3. Attached to the bearing axle 9 is a frame 10; approximately in the center of this frame 10, a mounting 11 is provided which serves to hold the upper jaw model. Vertically below the mounting 11, another mounting 12 is arranged in the base plate 5; this mounting 12 serves to hold the lower jaw model. At the free front end of the frame 10, a needle 13 is attached perpendicular to the plane of the frame. This needle 13 supports itself with its lower tip upon a cam disk 14 of the base 2. The needle 13 is arranged in the upper structure 3 such that it can be moved and is locked into the position required by means of a set screw 15. This needle 13 serves to align the upper structure with the base.

Figure 3:
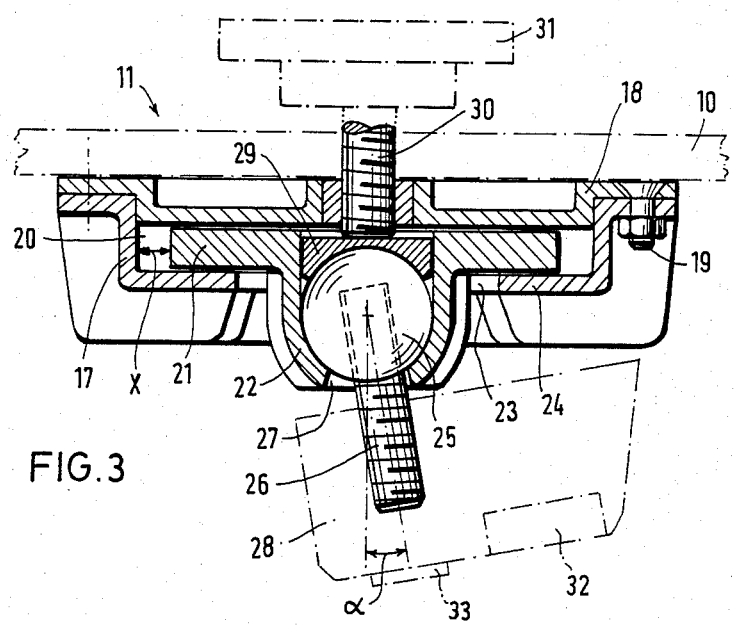
FIG. 3 shows a sectional view along the plane III—III in FIG. 2.

FIG. 3 gives a detailed representation of the design according to this invention of the mounting 11. The mounting 11 consists of a housing 17, the top of which can be closed by means of a cover 18. The cover 18 is fastened to the housing by means of screw 19. The internal chamber 20 holds a disk-shaped component 21 which can be moved. It is preferable for the internal chamber 20 to be circular; this also applies to the disk-shaped component. In the center of the disk-shaped component 21, an extension 22 is attached which protrudes through a lower opening 23 in the bottom of the housing 24. The extension 22 is designed as a hinged socket which holds a ball 25 such that the extension 22, together with the ball 25, forms a ball-and-socket joint. An extension arm bolt 26 is screwed into the ball 25. This extension arm bolt 26 extends through an opening 27 in the extension 22. At the end of the extension arm bolt 26, a shoe 28 is fastened which serves as the connection to the jaw model, which is not shown in the figure. The jaw model, which fits into the shoe 28, is shown in FIG. 5. Above the ball 25 in the internal chamber of the extension 22, a shim 29 is arranged. The contacting surface of the shim conforms to the surface of the ball such that it has a spherical shape. In the cover 18 above the shim 29, there is a threaded bolt 30 which extends through the cover 18. At the upper end of the threaded bolt 30, a disk 31 is attached which serves as a handle. When turning the threaded bolt 30, the front surface of this bolt pushes against the shim 29 and presses it against the ball 25. This causes the ball to be pressed against the interval wall of the extension 22 and thus locks it into the position desired. By means of the pressure exerted by the threaded bolt 30, the disk-shaped component 21 is also pressed against the housing bottom 24. This ensures that both the disk-shaped component 21 as well as the ball 25 can be stopped and locked in position in the housing 17. By screwing the threaded bolt 30 upward out of the cover, the locked position is released and both the disk-shaped component 21, as well as the ball 25, can move freely. The external diameter of the disk-shaped component 21 is 2 times smaller, relative to the sliding path desired in each case, than the internal diameter of the internal chamber 20. The sliding path X is marked in FIG. 3 by the double arrow. Moreover, the opening 23 in the extension 22 has a diameter such that the internal diameter of the opening 23 is 2 times larger, relative to the swivel path of the extension arm bolt 26, than the external diameter thereof. It is preferable for the pivoting angle α of the extension arm bolt from the perpendicular position to be 12°. The thickness of the disk-shaped component 21 is such that it can be positioned in the housing 17 free from play relative to its upper structure and its base. In order to ensure that the threaded bolt 30 cannot be released when the disk-shaped component 21 and the ball 25 are in locked positions, a locking device for this bolt may be provided on the housing.

Preferably, the shoe 28 has a parabolic circumference. The parabolic lateral walls are conically slanted downward, such that the upper surface is larger than the lower surface of the shoe 28. In the lower surface of the shoe 28, a magnetic plate 32 is inserted. Moreover, a centering shoulder 33 is provided on the lower surface.

As can be seen from FIG. 1, the mounting 12 in the lower structure also consists of a shoe 35 whose design corresponds precisely to the shoe 28 but whose position relative to the shoe 28 is rotated by 180°. The shoe 35 is attached to the lower structure such that the height of its position can be adjusted, this also means that the distance to the upper mounting 11 is adjustable, and the position of the shoe 35 can be locked into the position desired. Thus, the lower dental model can be quickly and easily mounted; due to the possibility of adjustment, an exact positioning in the articulator according to this invention is possible.

FIG. 5 shows a base mold 41 according to this invention which is a preformed component and which serves as a model base for a working or sawing model for working on dentures and which consists of a mold 42 which is adapted to the size of the jaw. This mold 42 is designed as a solid plastic piece which resists deformation. Such a base mold 41 as described by this invention has already been described in great detail in German Patent Application No. P 28 56 963.3. The mold 42 has an outer wall 43 which exhibits one central part which is rounded off and two parts which are positioned on the opposite side and which are flattened along the sides; the mold also has an internal wall 44 which is approximately parabolic, as well as a back wall 45 which closes the mold on the back. The walls 43, 44 and 45 enclose a hollow chamber 46 which approximately corresponds to the dental model; this hollow chamber extends upward such that its cross-section exhibits a profile which is approximately that of a truncated cone. Small ribs 49 are designed into the internal walls of the hollow chamber 47 and 48. Between the back wall 45 and the external surface of the internal wall 44, a horizontal plate 52 is located which is displaced upward relative to the lower edges of the walls 44 and 45 and which is preferably flush with the upper edges. The dimensions of this displaced part are such that its height corresponds to the shoe 28. Thus, the shoe 28 completely fills the chamber located below the plate 52. In the plate 52, a permanent magnet 53 is located; furthermore, a centering groove 54 is provided which fits the centering shoulder 33 in the shoe. By means of the magnet 53, which acts together with the magnetizable plate 32 in the shoe 28, the base mold is attached to the shoe 28, with the alignment being implemented by means of fitting the centering shoulder 33 into the groove 54. In order to fasten the base mold to the mounting 35 on the base, the base mold must be rotated 180° out of the position shown in FIG. 5.

FIG. 6 shows a practical example for the arrangement of the shoe 35, this arrangement being adjustable in height. As can be seen, the shoe 35 is attached to the upper end of a toothed shaft 56. This attachment may be effected either by slipping the shoe onto the toothed shaft or by screwing it on. The toothed shaft is guided in a housing 57 which is attached to the base plate 5. A pistion 58 which slides within a cylinder 59 of a cylinder projection 60 of the housing 57, serves as a guide for the toothed shaft 56 in the housing 57; this piston 58 is located on the lower end of the toothed rack 56. The cylinder projection 60 is inserted into the base plate 5 and there locked into position. A cogwheel 62, which is fastened to one end of rotating axis 63, this end being located on the housing 57, meshes with the teeth 61 of the toothed shaft 56. The rotating axis 63 extends horizontally into the housing 57 and is carried in such a way that it cannot be displaced; moreover, it exhibits a knob 64 on the end jutting out of the housing 57. By means of rotating the cogwheel 62, it is thus possible to adjust the height of the shoe 35 via the toothed shaft 56. Furthermore, a locking device is provided in order to lock the shoe 35 into the height position desired. This locking device consists of a locking screw 66 which is guided in a horizontal tapped hole 65 of the housing 57. The tapped hole 65 runs perpendicular to one of the lateral surfaces 67 of the toothed shaft 56. By screwing the locking screw 66 into the tapped hole 65 until its internal end comes into contact with the respective lateral surface 67 of the toothed shaft 56, the toothed shaft can be fixed into position by appropriately tightening the locking screw 66. The external end of the locking screw 66 extends out of the tapped hole 65 and its screwhead is designed as a knob 68, thus making it possible to manually tighten and loosen the locking screw quite easily.

The toothed shaft 56 has flat lateral surfaces 67 facing each other such that the cross section of the toothed shaft is approximately rectangular, however with the lateral surface opposite the teeth 61 forming a slightly convex curve. The housing has a guide opening which is adapted to the shape of the toothed shaft 56. Preferably, the toothed shaft 56 has helical teeth and its adjustment range is approximately 10 mm.

FIG. 9 shows a mounting plate 71 which can be used as an alternative to the shoe 28 or 35 and whose purpose it is to hold the plaster models. The mounting plate 71 consists of a carrier plate 72 whose outline has the approximate shape of the plaster model; it is recommended that this mounting plate have two lateral stops 73 and 74 which are located on the front of its two inward-slanting lateral sections, respectively. The lateral back section 76 of the carrier plate exhibits a fixing screw 77 which is guided in a bearing projection 78; for this purpose, this bearing projection has a tapped hole through which the fixing screw 77 extends. By setting a plaster cast onto the carrier plate 72 and by pushing its front surface against the two stops 73 and 74 and by subsequently turning the free end of the fixing screw against the back area of the plaster cast and tightening it, a secure attachment of the plaster cast onto the mounting plate 71 can be ensured. The two stops 73 and 74 preferably consist of two supporting angle pieces whose vertical end edges 79 can be easily pressed into the plaster cast when the plaster cast comes into contact with them. The free end of the fixing screw 77 preferably exhibits a pressure contact devie 80 which is connected flexibly with the fixing screw 77, preferably via some type of a ball-and-socket joint 81. The pressure contacting surface 82 of the pressure contact device 80 should be roughened or have small projections which can press into the plaster model as well. It is also possible for the stops 73 and 74 to be adjustably fastened to the carrier plate 72. It is also within the framework of this invention to provide fixing screws instead of the stops shown in the practical example, and to substitute a stop for the fixing screw. In the carrier plate 72, a screwed socket 83 is found which serves to attach the mounting plate to the upper structure and the base.

This invention is not restricted to the practical examples described here, but extends to all devices which operate within the scope and meaning of this invention.

The mountings 11 and 12 may consist of metal, but a suitable plastic may be used as well; this also applies to the other individual components of the mountings.

We claim:
1. In a base mold for the manufacture of a dental working model for working on dentures, the base mold having a hollow chamber adapted to receive the dental models, the chamber having a pair of internal walls and ribs on both internal walls, these ribs serving to form retention marks, with the hollow chamber becoming wider from the bottom to the top, and the base mold having a back wall spaced apart from the hollow chamber, the improvement comprising:
   a substantially parabolic horizontal plate affixed to the base mold between the back wall thereof and the internal wall next adjacent to said back wall;
   the base mold having a lower edge, and said horizontal plate being displaced upward relative to the lower edge of the base mold, and having a lower surface, thereby defining a receptacle bounded in part by said back wall, said internal wall next adjacent to the back wall, and the lower surface of the horizontal plate; and
   a permanent magnet inserted in the lower surface of said horizontal plate,
   so as to attract and retain the base mold to a magnetic plate mounted in a mounting shoe or the like, when the mounting shoe is disposed in said receptacle.
2. Apparatus as in claim 1, wherein:
   the lower surface of said horizontal plate has a centering groove in predetermined location for alignment with a centering shoulder on the mounting shoe, when the base mold is magnetically retained on the mounting shoe.
3. Apparatus as in claim 1, wherein said ribs in the chamber are of equal height.
4. Apparatus as in claim 1, wherein said chamber is open on both sides.
5. Apparatus as in claim 1, wherein the displacement of said horizontal plate relative to the lower edge of the base mold corresponds to the height of the mounting shoe intended to be received in said receptacle.
6. A base mold defining a hollow chamber for receiving a dental model and adapted for removable support on a mounting shoe, comprising:
   an internal wall having an internal surface defining the hollow chamber, and having an external surface;
   a back wall in spaced apart confronting relation to the external surface of said internal wall;
   a horizontal plate joining an end of said back wall and an end of said internal wall so as to define a receptacle between the two walls;
   said receptacle being open on the side remote from said horizontal plate, and configured to removably receive the mounting shoe through said open side;
   said horizontal plate having an inner surface facing said receptacle; and
   a permanent magnet disposed on said inner surface to attract and retain a mounting shoe when disposed in said receptacle.

* * * * *